(12) United States Patent
Zargari et al.

(10) Patent No.: US 11,795,462 B2
(45) Date of Patent: *Oct. 24, 2023

(54) THERAPY

(71) Applicant: INDEX PHARMACEUTICALS AB, Solna (SE)

(72) Inventors: Arezou Zargari, Stockholm (SE); Charlotte Admyre, Stockholm (SE); Pernilla Sandwall, Stockholm (SE); Thomas Knittel, Stockholm (SE); Peter Zerhouni, Stockholm (SE)

(73) Assignee: Index Pharmaceuticals AB, Solna (SE)

( * ) Notice: Subject to any disclaimer, the term of this patent is extended or adjusted under 35 U.S.C. 154(b) by 217 days.

This patent is subject to a terminal disclaimer.

(21) Appl. No.: 16/612,313

(22) PCT Filed: May 9, 2018

(86) PCT No.: PCT/EP2018/062140
§ 371 (c)(1),
(2) Date: Nov. 8, 2019

(87) PCT Pub. No.: WO2018/206722
PCT Pub. Date: Nov. 15, 2018

(65) Prior Publication Data
US 2020/0239893 A1 Jul. 30, 2020

(30) Foreign Application Priority Data

May 10, 2017 (GB) ..................................... 1707503

(51) Int. Cl.
*C12N 15/113* (2010.01)
*A61P 1/04* (2006.01)
*A61K 9/00* (2006.01)

(52) U.S. Cl.
CPC ........ *C12N 15/1138* (2013.01); *A61K 9/0031* (2013.01); *A61P 1/04* (2018.01); *C12N 2310/313* (2013.01); *C12N 2310/315* (2013.01); *C12N 2320/32* (2013.01); *C12N 2320/35* (2013.01)

(58) Field of Classification Search
CPC .......... C12N 15/1138; C12N 2310/313; C12N 2310/315; C12N 2320/32; C12N 2320/35; A61P 1/04; A61K 9/0031
See application file for complete search history.

(56) References Cited

U.S. PATENT DOCUMENTS

| | | | |
|---|---|---|---|
| 5,366,878 A | 11/1994 | Pederson et al. | |
| 5,635,377 A | 6/1997 | Pederson et al. | |
| 8,148,341 B2* | 4/2012 | Spiik | A61P 17/06 536/23.1 |
| 8,258,107 B2* | 9/2012 | Lofberg | A61P 11/06 536/23.1 |
| 8,569,257 B2* | 10/2013 | Spiik | A61P 11/00 536/23.1 |
| 8,592,390 B2* | 11/2013 | Lofberg | A61K 31/56 536/23.1 |
| 9,492,516 B2* | 11/2016 | Admyre | A61P 37/02 |
| 9,795,627 B2* | 10/2017 | Admyre | A61K 45/06 |
| 2015/0004187 A1* | 1/2015 | Admyre | A61P 1/04 424/185.1 |
| 2019/0321613 A1* | 10/2019 | Jones | A61B 5/0084 |

FOREIGN PATENT DOCUMENTS

| | | |
|---|---|---|
| AU | 2012200661 | 3/2012 |
| WO | WO2007004977 | 1/2007 |
| WO | WO2011078672 | 6/2011 |
| WO | WO2013076262 | 5/2013 |

OTHER PUBLICATIONS

Atreya et al (The Lancet, 2020. doi: https://doi.org/10.1016/S2468-1253(20)30301-0) (Year: 2020).*
Anonymous, "The Efficacy of Cobitolimod in Patients With Moderate to Severe Active Ulcerative Colitis (CONDUCT)," U.S. National Library of Medicine 2017, 1-8.
Atreya et al., "Clinical Effects of a Topically Applied Toll-like Receptor 9 Agonist in Active Moderate-to-Severe Ulcerative Colitis," Journal of Crohn's and Colitis 2016, 1294-1302.
D'Haens et al., "A Review of Activity Indices and Efficacy End Points for Clinical Trials of Medical Therapy in Adults With Ulcerative Colitis," Gastroenterology 2007, 132, 763-786.
Domenech et al., "An Overview of the Natural History of Inflammatory Bowel Diseases," Digestive Diseases 2014, 32(4), 320-327.
Fausel et al., "Biologies in the management of ulcerative colitis—comparative safety and efficacy of TNF-α antagonists," Therapeutics and Clinical Risk Management 2015, 11, 63-73.
FDA, "Ulcerative Colitis: Clinical Trial Endpoints Guidance for Industry," U.S. Department of Health and Human Services Food and Drug Administration CDER 2016.
Galvez, "Role of Th17 Cells in the Pathogenesis of Human IBD," ISRN Inflammation 2014, 928461.
Geboes et al., "A reproducible grading scale for histological assessment of inflammation in ulcerative colitis," Gut 2000, 47, 404-409.
Gong et al., "The Th17/Treg Immune Balance in Ulcerative Colitis Patients with Two Different Chinese Syndromes: Dampness-Heat in Large Intestine and Spleen and Kidney Yang Deficiency Syndrome," Evidence-Based Complementary and Alternative Medicine 2015, 264317.

(Continued)

*Primary Examiner* — Richard A Schnizer
(74) *Attorney, Agent, or Firm* — Sheppard, Mullin, Richter & Hampton LLP

(57) ABSTRACT

The present invention provides an oligonucleotide comprising the sequence 5'-GGAACAGTTCGTCCATGGC-3' (SEQ ID NO:2) for use in the treatment of inflammatory bowel disease in a human subject, wherein individual doses of from 100 mg to 350 mg of said oligonucleotide are administered to the subject on at least four separate occasions, wherein the separate occasions are each a week apart.

19 Claims, 5 Drawing Sheets
Specification includes a Sequence Listing.

(56) References Cited

OTHER PUBLICATIONS

Irvine, "Quality of Life of Patients with Ulcerative Colitis: Past, Present, and Future," Inflammatory Bowel Disease 2008, 14(4), 554-565.

Khan et al., "Efficacy of Immunosuppressive Therapy for Inflammatory Bowel Disease: A Systematic Review and Meta-Analysis," American Journal of Gastroenterology 2011, 106(4), 630-642.

Kim et al., "Myeloid-Derived Suppressor Cells in Inflammatory Bowel Disease," Intestinal Research 2015, 13(2), 105-111.

Kuznetsov et al., "Biomarkers can predict potential clinical responders to DIMS0150 a toll-like receptor 9 agonist in ulcerative colitis patients," BMC Gastroenterology 2014, 14(79), 1-16.

Love, "Pharmacotherapy for Moderate to Severe Inflammatory Bowel Disease: Evolving Strategies," American Journal of Managed Care 2016, 22(3), S39-S50.

Musch et al., "Topical Treatment with the Toll-like Receptor Agonist DIMS0150 Has Potential for Lasting Relief of Symptoms in Patients with Chronic Active Ulcerative Colitis by Restoring Glucocorticoid Sensitivity," Inflammatory Bowel Disease 2013, 19(2), 283-292.

Pedersen et al., "Expression of Toll-like receptor 9 and response to bacterial CpG oligodeoxynucleotides in human intestinal epithelium*," Clinical and Experimental Immunology 2005, 141, 298-306.

Peyrin-Biroulet et al., "Defining Disease Severity in Inflammatory Bowel Diseases: Current and Future Directions," Clinical Gastroenterology and Hepatology 2016, 14(3), 348-354.

Prantera et al., "Glucocorticosteroids in the treatment of inflammatory bowel disease and approaches to minimizing systemic activity," Therapeutic Advances in Gastroenterology 2013, 6(2), 137-156.

Rachmilewitz, "Coated mesalazine (5-aminosalicylic acid) versus sulphasalazine in the treatment of active ulcerative colitis: a randomised trial," BMJ 1989, 298, 82-86.

Shroeder et al., "Coated Oral 5-Aminosalicylic Acid Therapy for Mildly to Moderately Active Ulcerative Colitis," The New England Journal of Medicine 1987, 317(26), 1625-1629.

Strange et al., "European evidence-based Consensus on the diagnosis and management of ulcerative colitis: Definitions and diagnosis," Journal of Crohn's and Colitis 2008, 2, 1-23.

Sutherland et al., "5-Aminosalicylic Acid Enema in the Treatment of Distal Ulcerative Colitis, Proctosigmoiditis, and Proctitis," Gastroenterology 1987, 92, 1894-1898.

Travis et al., "Review article: defining remission in ulcerative colitis," Alimentary Pharmacology and Therapeutics 2011, 34, 113-124.

Travis et al., "European evidence-based Consensus on the management of ulcerative colitis: Current management," Journal of Crohn's and Colitis 2008, 2, 24-62.

Ungar et al., "Advances in the development of new biologies in inflammatory bowel disease," Annals of Gastroenterology 2016, 29, 1-6.

Vegter et al., "Meta-analysis using individual patient data: efficacy and durability of topical alicaforsen for the treatment of active ulcerative colitis," Alimentary Pharmacology and Therapeutics 2013, 38, 284-293.

Atreya et al., "Clinical disease activity influences the therapeutic efficacy of the toll like receptor-9 agonist cobitolimod in patients with moderate to severe active ulcerative colitis", United European Gastroenterology Journal 2016, 4(5S), A46, Abstract No. OP107.

Feagan et al., "Vedolizumab as Induction and Maintenance Therapy for Ulcerative Colitis," The New England Journal of Medicine 2013, 369(8), 699-710.

Sandborn et al., "Tofacitinib as Induction and Maintenance Therapy for Ulcerative Colitis," The New England Journal of Medicine 2017, 376(18), 1723-1736.

Yarlas et al., "The Inflammatory Bowel Disease Questionnaire in Randomized Controlled Trials of Treatment for Ulcerative Colitis: Systematic Review and Meta-Analysis," Journal of Patient-Centered Research and Reviews 2020, 7(2), 189-205.

* cited by examiner

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: SEQ ID NO: 1 Cobitolimod
<220> FEATURE:
<221> NAME/KEY: misc_feature
<222> LOCATION: (1)..(4)
<223> OTHER INFORMATION: phosphorothioate linkage between bases: 1-2, 2-
```

```
                                     3 and 3-4
<220> FEATURE:
<221> NAME/KEY: misc_feature
<222> LOCATION: (16)..(20)
<223> OTHER INFORMATION: phosphorothioate linkage between bases: 16-17,
      17-18 and 18-19

<400> SEQUENCE: 1
ggaacagttc gtccatggc                                                    19

<210> SEQ ID NO 2
<211> LENGTH: 19
<212> TYPE: DNA
<213> ORGANISM: Artificial Sequence
<220> FEATURE:
<223> OTHER INFORMATION: SEQ ID NO: 2 - synthesised oligonucleotide

<400> SEQUENCE: 2
ggaacagttc gtccatggc                                                    19
```

THERAPY

CROSS-REFERENCE TO RELATED APPLICATIONS

This application is the U.S. National Phase Application under 35 U.S.C. § 371 of International Application No. PCT/EP2018/062140, filed on May 9, 2018, designating the U.S. and published in English as WO 2018/206722 A1 on Nov. 15, 2018, which claims the benefit of priority to GB Patent Application No. 1707503.7, filed on May 10, 2017. The disclosures of these related applications are herein expressly incorporated by reference in their entireties, including any drawings.

REFERENCE TO SEQUENCE LISTING

The present application is being filed along with a Sequence Listing in electronic format. The Sequence Listing is provided as a file entitled "N408171WOSequenceListingMay2018_ST25", created Nov. 8, 2019, which is approximately 4 KB in size, and updated by a Replacement Electronic Sequence Listing file entitled "Amended_sequence_listing_N408171US_HCB_EGH_ST25", created on Apr. 2, 2020, which is 4 KB in size. The information in the electronic format of the Sequence Listings is incorporated herein by reference in its entirety.

FIELD OF THE INVENTION

The present invention relates to new therapies for treating inflammatory bowel diseases, for instance active ulcerative colitis (UC), wherein an oligonucleotide, especially cobitolimod, is administered according to an optimised dosage regime.

BACKGROUND OF THE INVENTION

Ulcerative colitis (UC) is a disease characterized by chronic inflammation of the rectal and colonic mucosa, affecting the innermost lining in the first stage. The disease is recurrent, with both active and inactive stages that differ in pathology, symptoms and treatment. The underlying cause of UC is not understood, nor is it known what triggers the disease to recur between its inactive and active forms (Irvine, E. J. (2008) Inflamm Bowel Dis 14(4): 554-565). Symptoms of active UC include progressive loose stools with blood and increased frequency of bowel movements. Active mucosal inflammation is diagnosed by endoscopy.

The stools contain pus, mucous and blood and are often associated with abdominal cramping with urgency to evacuate (tenesmi). Diarrhoea may have an insidious onset or, more rarely, start quite suddenly. In severe cases the symptoms may include fever and general malaise. In severe stages, deep inflammation of the bowel wall may develop with abdominal tenderness, tachycardia, fever and risk of bowel perforation. Furthermore, patients with UC may suffer extra intestinal manifestations such as arthralgia and arthritis, erythema nodosum, pyoderma gangrenosum and inflammation in the eyes. In the case of remission or inactive UC, patients are usually free of bowel symptoms.

The extent of inflamed and damaged mucosa differs among patients with UC. UC that affects only the rectum is termed ulcerative proctitis. The condition is referred to as distal or left sided colitis when inflammatory changes are present in the left side of the colon up to the splenic flexure. In extensive UC the transverse colon is also affected, and pancolitis designates a disease involving the entire colon.

Active mucosal inflammation is diagnosed by endoscopy and is characterized by a loss of vascular patterning, oedema, petechia, spontaneous bleeding and fibrinous exudates. The endoscopic picture is that of continuous inflammation, starting in the rectum and extending proximally to a variable extent into the colon. Biopsies obtained at endoscopy and subjected to histological examination help to diagnose the condition. Infectious causes, including *Clostridium difficile*, camphylobacter, *Salmonella* and *Shigella*, may mimic UC and can be excluded by stool cultures.

The medical management of UC is divided into treatment of active disease and maintenance of remission.

The treatment of patients with active UC aims to reduce inflammation and promote colon healing and mucosal recovery. In milder cases the disease may be controlled with conventional drugs including sulphasalazine, 5-aminosalicylic acid (5-ASA) (Sutherland, L., F. Martin, S. Greer, M. Robinson, N. Greenberger, F. Saibil, T. Martin, J. Sparr, E. Prokipchuk and L. Borgn (1987) Gastroenterology 92: 1894-1898) and glucocorticosteroids (GCS) (Domenech, E., M. Manosa and E. Cabre (2014). Dig Dis 32(4): 320-327).

GCS are generally used to treat disease flare-ups and are not recommended for maintenance of remission since there are significant side effects in long-term use, and the possible development of steroid dependent disease. Glucocorticoid drugs act non-selectively, so in the long run they may impair many healthy anabolic processes. As a result, maintenance treatment with systemic GCS is not advised (Prantera, C. and S. Marconi (2013) Therap Adv Gastroenterol 6(2): 137-156).

For patients who become refractory to GCS and suffer from severe or moderately severe attacks of UC, the addition of immunomodulatory agents such as cyclosporine, 6-mercaptopurine and azathioprine may be used. However, immunomodulators are slow-acting and the induction of remission in these patients is often temporary (Khan, K. J., M. C. Dubinsky, A. C. Ford, T. A. Ullman, N. J. Talley and P. Moayyedi (2011) Am J Gastroenterol 106(4): 630-642).

Further treatment options for UC include biologic agents (Fausel, R. and A. Afzali (2015) Ther Clin Risk Manag 11: 63-73). The three TNF-α inhibitors currently approved for the treatment of moderate to severe UC are infliximab, adalimumab, and golimumab. All three carry potential risks associated with their use, and should be avoided in certain patients, e.g. those with uncontrolled infections, advanced heart failure, neurologic conditions and in patients with a history of malignancy, due to a potential risk of accelerating the growth of a tumour. Other potential adverse effects of TNF-α inhibitor therapy include neutropenia, hepatotoxicity, serum sickness, leukocytoclastic vasculitis, rash including psoriasiform rash, induction of autoimmunity, and injection or infusion site reactions, including anaphylaxis, convulsions, and hypotension.

All three TNF-α inhibitor agents and their related biosimilar/derivative counterparts may be used to induce and maintain clinical response and remission in patients with UC. Combination therapy with azathioprine is also used for inducing remission.

However, more than 50% of patients receiving TNF-α inhibitor agents fail to respond to induction dosing, or lose response to the TNF-α inhibitor agents over time (Fausel, R. and A. Afzali (2015) Ther Clin Risk Manag 11: 63-73).

Vedolizumab, a α4β7 integrin inhibitor, was recently approved for the treatment of UC. In the GEMINI 1 trial, vedolizumab was found to be more effective than placebo for inducing and maintaining clinical response, clinical remission, and mucosal healing (Feagan, B. G., P. Rutgeerts, B. E. Sands, S. Hanauer, J. F. Colombel, W. J. Sandborn, G. Van Assche, J. Axler, H. J. Kim, S. Danese, I. Fox, C. Milch, S. Sankoh, T. Wyant, J. Xu, A. Parikh and G. S. Group (2013). "Vedolizumab as induction and maintenance therapy for ulcerative colitis." N Engl J Med 369(8): 699-710.).

Ulcerative colitis patients, who are chronically active and refractory to known treatments pose a serious medical challenge and often the only remaining course of action is colectomy. A total colectomy is a potentially curative option in severe UC, but is a life-changing operation that entails risks as complications, such as pouch failure, pouchitis, pelvic sepsis, infertility in women, and nocturnal faecal soiling, may follow. Therefore, surgery is usually reserved for patients with severe refractory disease, surgical or other emergencies, or patients with colorectal dysplasia or cancer.

An emergent third line treatment for UC is cobitolimod (Kappaproct/DIMS0150), a modified single strand deoxyribonucleic acid (DNA)-based synthetic oligonucleotide of 19 bases in length. Cobitolimod has the sequence 5'-G*G*A*ACAGTTCGTCCAT*G*G*C-3' (SEQ ID NO:1), wherein the CG dinucleotide is unmethylated.

Cobitolimod functions as an immunomodulatory agent by targeting the Toll-like receptor 9 (TLR9) present in immune cells. These immune cells (i.e., B-cells and plasmacytoid dendritic cell (pDCs) reside in high abundance in mucosal surfaces, such as colonic and nasal mucosa. The immune system is the key mediator of the changes of UC. The mucosa of the colon and rectum of patients with UC is chronically inflamed and contains active immune cells. Cobitolimod may be topically administered in the region of inflammation, which places the drug in close contact with a high number of intended target cells, ensuring that the drug will reach an area rich in TLR9 expressing cells. The activation of these cells by cobitolimod induces various cytokines, such as type I interferons and interleukin 10 (IL-10) which are classical anti-inflammatory cytokines and are believed to be important factors for the clinical effect of cobitolimod.

A range of non-clinical safety studies have been conducted with cobitolimod, as well as four clinical trials. The majority of the trials have involved administration of a relatively low (30 mg) dose of cobitolimod. Overall, data on cobitolimod support a positive benefit-risk assessment for patients with chronic active UC. Cobitolimod is safe and well tolerated and has been shown to be effective to induce clinical response and remission in patients with chronic active UC, as well as symptomatic and endoscopic remission in patients with treatment refractory, moderate to severe chronic active UC.

There now exists a need for improved dosage regimes for cobitolimod that maximise its efficacy/safety profile for clinical use.

SUMMARY OF THE INVENTION

It has now surprisingly been found that, for treatment of inflammatory bowel diseases such as UC, administration of cobitolimod at a dosage of from 100 mg to 350 mg, preferably 100 mg to 150 mg, more preferably around 125 mg, on at least four, preferably four, separate occasions each a week apart is optimal, for instance to induce remission. The increase in efficacy of the drug at 125 mg and 250 mg is more than would have been expected from the previous clinical studies carried out at much lower doses.

The present invention therefore provides an oligonucleotide comprising the sequence 5'-GGAACAGTTCGTC-CATGGC-3' (SEQ ID NO:2) for use in the treatment of inflammatory bowel disease in a human subject, wherein individual doses of from 100 mg to 350 mg of said oligonucleotide are administered to the subject on at least four separate occasions, wherein the separate occasions are each a week apart.

The present invention also provides a pharmaceutical composition comprising an oligonucleotide as defined herein, together with one or more pharmaceutically acceptable carriers, for use in the treatment of inflammatory bowel disease as defined herein in a human subject as defined herein, wherein individual administrations of said composition are administered to the subject on at least four separate occasions, wherein the separate occasions are each a week apart, and wherein each administration of the composition delivers an amount of the oligonucleotide as defined herein.

The present invention also provides a method of treating inflammatory bowel disease as defined herein, in a human subject as defined herein, comprising administering to said subject an oligonucleotide as defined herein or a composition as defined herein, wherein individual administrations of said oligonucleotide or composition are administered to the patient on at least four separate occasions, wherein the separate occasions are each a week apart, and wherein each administration of the oligonucleotide or composition delivers an amount of the oligonucleotide as defined herein.

In preferred embodiments, the oligonucleotide has the sequence 5'-G*G*A*ACAGTTCGTCCAT*G*G*C-3' (SEQ ID NO:1), wherein the CG dinucleotide is unmethylated. Thus, in preferred embodiments, the oligonucleotide is cobitolimod.

DETAILED DESCRIPTION OF THE INVENTION

Figure 1:
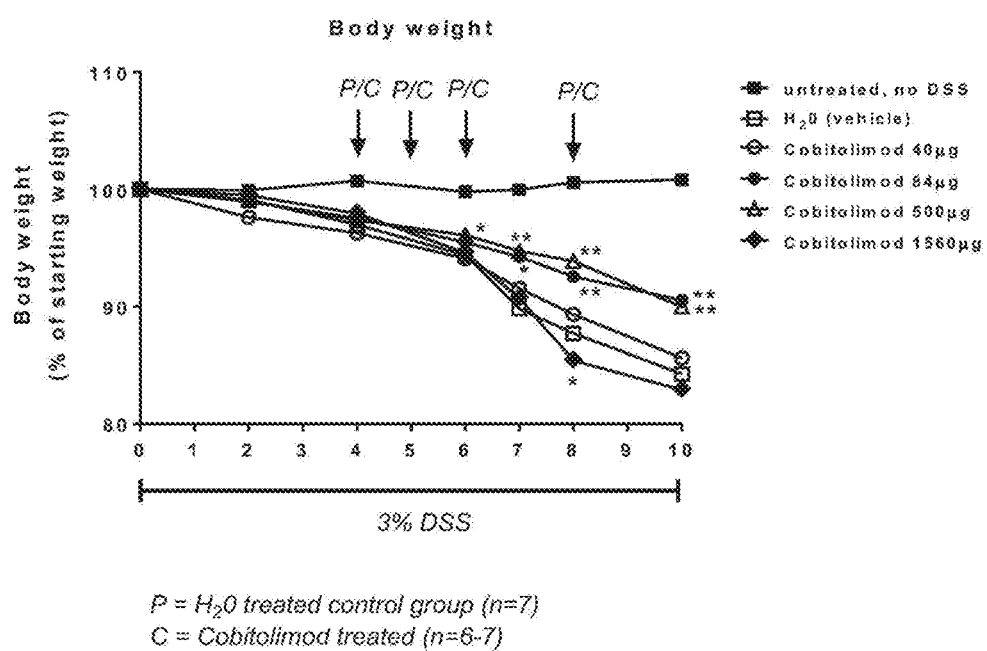
FIG. 1 shows the results for weight loss in mice in a DSS-induced colitis mouse model over 10 days.

All patents, patent applications, and publications cited herein are hereby incorporated by reference in their entirety.

As used herein, the term "subject" refers to a human subject/patient. The terms "subject" and "patient" are used interchangeably herein.

As used herein, the term inflammatory bowel disease (IBD) refers to a group of inflammatory conditions of the colon and the gastrointestinal tract. The major types of IBD are ulcerative colitis (UC) and Crohn's disease. The main difference between UC and Crohn's disease is the location and nature of the inflammatory changes. Crohn's disease can affect any part of the gastrointestinal tract, from mouth to anus, while UC is restricted to the colon and the rectum. In some cases, a definitive diagnosis of either Crohn's disease or UC cannot be made due to idiosyncrasies in the presentation. In these cases a diagnosis of indeterminate colitis may be made. Other forms of IBD include, but are not limited to, collagenous colitis, lymphocytic colitis, ischaemic colitis, diversion colitis, Behçet's disease and indeterminate colitis.

Typically, the inflammatory bowel disease is ulcerative colitis (UC).

The disease ulcerative colitis (UC) is well known to one skilled in the art. Ulcerative colitis treated in accordance with the present invention may involve treatment of ulcerative proctitis, distal or left sided colitis, extensive colitis, pancolitis and pouchitis.

Patients with UC typically present with a spectrum of disease severity ranging from remission to severely active. Clinical assessment can be used to classify UC patients into 4 disease activity subgroups as defined in D'Haens, Gastroenterology 2007; 132: 763-786, the entirety of which is incorporated herein by reference: (1) remission (≤2 or 3 stools/day, without the presence of blood and/or pus in the stools, with no systemic symptoms); (2) mildly active disease (3 or 4 stools/day and/or presence of blood and/or pus in the stools less than daily, with no systemic symptoms of fever or weight loss); (3) moderately active disease (>4 stools/day and/or daily presence of blood and/or pus) with minimal systemic symptoms; and (4) severely active disease (>6 bloody stools/day, and evidence of toxicity, as demonstrated by fever, tachycardia, anemia, or an erythrocyte sedimentation rate ESR).

Typically, the patient is suffering from moderate to severe UC. Preferably, the patient is suffering from moderate to severe UC as defined above.

As used herein, the words "treatment" and "treating" are to be understood as embracing treatment and/or amelioration and/or prevention of or reduction in aggravation/worsening of symptoms of a disease or condition as well as treatment of the cause of the disease or condition, and may include reversing, reducing, or arresting the symptoms, clinical signs, and underlying pathology of a condition in a manner to improve or stabilise a subject's condition.

In particular in the context of ulcerative colitis, "treating" typically refers to inducing response or remission in a patient having active ulcerative colitis. Thus, typically, the oligonucleotide is for inducing response or remission of active ulcerative colitis in a patient. Inducing response means improving the condition of a patient by e.g. reducing and/or arresting the symptoms and clinical signs of the active disease. Inducing remission means transitioning a patient from a state where they are considered to be in an active stage of the disease to a state where they are considered to be in remission.

Induction of response or remission in UC patients is typically assessed by one or more of endoscopy, histology, patient recorded outcomes and quality of life outcomes. Thus, reference to induction of response or remission includes induction of one or more of endoscopic remission, endoscopic response, histological remission, histological response, response or remission as determined by physician or by patient recorded outcomes, and response or remission as determined by quality of life. This can typically be assessed by reference to one or more standard indices.

Typically, ulcerative colitis is chronic active ulcerative colitis.

As used herein, the term "chronic active ulcerative colitis" refers to patients with ulcerative colitis that is both active and chronic. Active ulcerative colitis is typically as defined herein, i.e. the patient is not in remission. Chronic ulcerative colitis refers to a disease characterized by a chronic inflammation of the rectal and colonic mucosa.

Preferably, reference herein to "treating" refers to inducing response or remission in a patient having chronic active ulcerative colitis. Thus, typically, the oligonucleotide is for inducing response or remission of chronic active ulcerative colitis in a patient.

Induction of response or remission in UC patients may be determined in accordance with one or more standard disease indices. Typical disease indices include but not limited to the ones mentioned below; (i) disease activity determined by clinical and biochemical disease activity, (ii) disease activity determined by endoscopic disease activity, (iii) disease activity determined by composite clinical and endoscopic disease activity indices, (iv) quality of life, (v) histologic disease activity. These indices are discussed in D'Haens (ibid).

Indices based on disease activity determined by clinical and biochemical disease activity include the Truelove and Witts Severity Index; Powell-Tuck (St. Mark's) Index; Clinical Activity (Rachmilewitz) Index; Activity (Seo) Index; Physician Global Assessment; Lichtiger (Modified Truelove and Witts Severity) Index; Investigators Global Evaluation; Simple Clinical Colitis Activity Index; Improvement Based on Individual Symptom Scores; Ulcerative Colitis Clinical Score; and Patient-defined remission. These indices are discussed in D'Haens (ibid).

Indices based on disease activity determined by endoscopic disease activity include the Truelove and Witts Sigmoidoscopic Assessment; Baron score; Powell-Tuck Sigmoidoscopic Assessment; Endoscopic (Rachmilewitz Endoscopic) Index; Sigmoidoscopic Index; Sigmoidoscopic Inflammation Grade Score; Mayo Score Flexible Proctosigmoidoscopy Assessment; Sutherland Mucosal Appearance Assessment; and Modified Baron Score. These indices are discussed in D'Haens (ibid).

Indices based on disease activity determined by composite clinical and endoscopic disease activity indices include the Mayo Score (Mayo Clinic Score/Disease Activity Index); Modified Mayo Score and Sutherland Index (Disease Activity Index/UC Disease Activity Index). Mayo Score and Sutherland Index are discussed in D'Haens (ibid).

Indices based on quality of life include the Rating Form of IBD Patient Concerns; and the Inflammatory Bowel Disease Questionnaire (IBDQ). These indices are discussed in D'Haens (ibid).

Indices based on histologic disease activity include those discussed in D'Haens (ibid) such as Geboes Index and Riley Index and further indices such as Nancy Index and Robarts Index.

Preferred indices for assessing UC patients include the Clinical Activity (Rachmilewitz) Index, Mayo Score and Modified Mayo Score.

The Clinical Activity (Rachmilewitz) Index is an index taking into account 7 variables: number of stools, blood in stools, investigator's global assessment of symptomatic state, abdominal pain or cramps, temperature due to colitis, extraintestinal manifestations, and laboratory findings. This is discussed further in D'Haens (ibid) and Rachmilewitz D., BMJ 1989; 298: 82-86, the entirety of which is incorporated herein by reference. Determination of the Clinical Activity (Rachmilewitz) Index produces a score for a patient ranging from 0 to 29 points (higher scores meaning more severe disease).

Clinical remission may be considered as a Clinical Activity (Rachmilewitz) Index score≤4 points. Response as determined by the Clinical Activity (Rachmilewitz) Index means the patient has a lower score after treatment than before treatment.

The Mayo Score is an index taking into account 4 items: stool frequency, rectal bleeding, findings of lower GI endoscopy, and Physician's Global Assessment (PGA). This is discussed further in D'Haens (ibid) and Schroeder K W et al, N Engl J Med 1987; 317: 1625-1629, the entirety of which is incorporated herein by reference. Determination of the Mayo Score produces a score ranging from 0 to 12 points (higher scores meaning more severe disease). In addition to the four specific items, a patient's functional assessment is also measured that is not meant to be included in the 12-point index calculation but should be used as a measure of general well-being when determining the PGA score.

Mayo scoring for each of the 4 items is determined as set out in the Table below.

Alternatively, clinical remission may be defined as a Mayo Score of 0 and clinical improvement (response) as a decrease from baseline in the Mayo Score≥3 points.

Alternatively, clinical remission may be defined as a Mayo Score of 0 and clinical improvement (response) as a decrease from baseline in the Mayo Score≥3 points (or a decrease of ≥2 points if the baseline Mayo Score was ≤3 points).

Alternatively, remission as determined by Mayo Score may be defined as requiring subscores of 0 for both sigmoidoscopy and rectal bleeding and a score of 0 or 1 for stool frequency and PGA subscores. Response may be defined as a decrease from baseline in the Mayo Score≥3 points; clinical response may be defined as a decrease from baseline in the Mayo Score (without the endoscopy subscore, also known as a Partial Mayo Score)≥2 points, and endoscopic response may be defined as a decrease from baseline in the endoscopic subscore≥1 point.

Alternatively, clinical remission may be defined as a total Mayo score of ≤2 points with no individual subscore>1 point, clinical response may be defined as a decrease from baseline in the total Mayo score≥3 points and ≥30% and a

| Score | Stool frequency[b] | Rectal Bleeding[c] | Physician's global assessment[d] | Colonoscopy/sigmoidoscopy finding |
|---|---|---|---|---|
| 0 | Normal number of stools for this patient | No blood seen | Normal or no disease | Normal or inactive disease |
| 1 | 1 to 2 stools more than normal | Streaks of blood with stool less than half of the time | Mild disease | Mild disease (erythema, decreased vascular pattern, mild friability) |
| 2 | 3 to 4 stools more than normal | Obvious blood with stool most of the time | Moderate disease | Moderate disease (marked erythema, lack of vascular pattern, friability, erosions) |
| 3 | 5 or more stools more than normal | Blood alone passed | Severe disease | Severe disease (spontaneous bleeding, ulceration) |

[b]Each patient serves as his or her own control to establish the degree of abnormality of the stool frequency.

[c]The daily bleeding score represents the most severe day of bleeding

[d]The physician's global assessment acknowledges the 3 other criteria, the patient's daily record of abdominal discomfort and general sense of well-being, and other observations, such as physical findings and the patient's performance status.

Remission according to the Mayo Score may be defined as complete resolution of (1) stool frequency (normal stool frequency), (2) rectal bleeding (no rectal bleeding), (3) patient's functional assessment score (generally well), (4) endoscopy findings (normal), and a PGA score of 0. Response as determined by Mayo Score typically requires improvement (a minimum 1-point decrease from baseline) in the PGA score and improvement in at least one other clinical assessment (stool frequency, rectal bleeding, patient's functional assessment, endoscopy findings) and no worsening in any other clinical assessment.

decrease in the rectal bleeding subscore≥1 point or an absolute rectal bleeding subscore of 0 or 1, and mucosal healing may be defined as an absolute endoscopy subscore of 0 or 1.

In one embodiment, patients having active ulcerative colitis have a Mayo Score>2. Patients who are in a remission phase of ulcerative colitis typically have a Mayo Score≤2.

Modified Mayo Score is related to the Mayo Score, which is defined above. Modified Mayo Score differs from Mayo Score in that the Colonoscopy/sigmoidoscopy scoring takes less account of friability. Thus, the scoring table for the Modified Mayo Score is as set out below.

| Score | Stool frequency[b] | Rectal Bleeding[c] | Physician's global assessment[d] | Colonoscopy/sigmoidoscopy finding |
|---|---|---|---|---|
| 0 | Normal number of stools for this patient | No blood seen | Normal or no disease | Normal or inactive disease |
| 1 | 1 to 2 stools more than normal | Streaks of blood with stool less than half of the time | Mild disease | Mild disease (erythema, decreased vascular pattern) |
| 2 | 3 to 4 stools more than normal | Obvious blood with stool most of the time | Moderate disease | Moderate disease (marked erythema, lack of vascular pattern, friability, erosions) |
| 3 | 5 or more stools more than normal | Blood alone passed | Severe disease | Severe disease (spontaneous bleeding, ulceration) |

[b]Each patient serves as his or her own control to establish the degree of abnormality of the stool frequency.
[c]The daily bleeding score represents the most severe day of bleeding
[d]The physician's global assessment acknowledges the 3 other criteria, the patient's daily record of abdominal discomfort and general sense of well-being, and other observations, such as physical findings and the patient's performance status.

Remission and response values for the Modified Mayo Score are as set out above for the Mayo Score. Modified Mayo Score is typically assessed in accordance with the FDA's draft guidance document "Ulcerative Colitis: Clinical Trial Endpoints Guidance for Industry" found at fda.gov/downloads/Drugs/GuidanceComplianceRegulatoryInformation/Guid ances/UCM515143.pdf Alternatively, Modified Mayo Score may differ from Mayo Score in that the Colonoscopy/sigmoidoscopy scoring takes less account of friability and also in that Physician's Global Assessment is not determinative. Thus, the scoring table for the Modified Mayo Score may also be as follows.

| Score | Stool frequency[b] | Rectal Bleeding[c] | Colonoscopy/sigmoidoscopy finding |
|---|---|---|---|
| 0 | Normal number of stools for this patient | No blood seen | Normal or inactive disease |
| 1 | 1 to 2 stools more than normal | Streaks of blood with stool less than half the time | Mild disease (erythema, decreased vascular pattern) |
| 2 | 3 to 4 stools more than normal | Obvious blood with stool most of the time | Moderate disease (marked erythema, lack of vascular pattern, friability, erosions) |
| 3 | 5 or more stools more than normal | Blood alone passed | Severe disease (spontaneous bleeding, ulceration) |

[b]Each patient serves as his or her own control to establish the degree of abnormality of the stool frequency.
[c]The daily bleeding score represents the most severe day of bleeding Remission and response values for this alternative Modified Mayo Score are typically as set out above for the Mayo Score. Alternatively, remission may be defined in accordance with this alternative Modified Mayo Score by subscores of i) rectal bleeding of 0, ii) stool frequency of 0 or 1 (with at least one point decrease from Baseline, Week 0), and iii) endoscopy score of 0 or 1 (excluding friability).

Induction of remission of UC may be in accordance with the criteria set out in S. P. L. Travis, Aliment Pharmacol Ther 2011; 34: 113-124, the entirety of which is incorporated herein by reference, i.e. complete cessation of rectal bleeding, urgency and increased stool frequency, preferably confirmed by endoscopic mucosal healing.

Alternatively, induction of response or remission may be in accordance with the criteria set out in E. F. Stange, Journal of Crohn's and Colitis (2008) 2, 1-23; S. P. L. Travis, Journal of Crohn's and Colitis (2008) 2, 24-62; K Geboes, Gut 2000; 47: 404-409; the entirety of which are incorporated herein by reference.

Induction of response or remission in Crohn's disease patients may be determined in accordance with one or more standard disease indices. Typical indices include the Crohn's Disease Activity Index (CDAI). The CDAI is discussed in Love, "Pharmacotherapy for Moderate to Severe Inflammatory Bowel Disease: Evolving Strategies", Am J Manag Care. 2016; 22:S39-S50; Peyrin-Biroulet et al "Defining disease severity in inflammatory bowel diseases: current and future directions" Clin Gastroenterol Hepatol. 2015; pii: S1542-3565(15)00787-00789. doi: 10.1016/j.cgh.2015.06.001; and Ungar et al "Advances in the development of new biologics in inflammatory bowel disease", Annals of Gastroenterology (2016) 29, 243-248. Alternative indices for assessing Crohn's disease patients include the Harvey-Bradshaw index and the Inflammatory Bowel Disease Questionnaire.

CDAI is a composite score taking into account a large number of symptoms associated with Crohn's disease, including number of liquid or soft stools; abdominal pain; general well being; presence of complications (the presence of joint pains (arthralgia) or frank arthritis; inflammation of the iris or uveitis; presence of erythema nodosum, pyoderma gangrenosum, or aphthous ulcers; anal fissures, fistulae or abscesses; other fistulae; fever during the previous week); use of lomotil or opiates for diarrhea; presence of an abdominal mass; hematocrit value; and percentage deviation from standard weight. Clinical remission according to the CDAI is typically indicated by a score of <150.

The subject treated in accordance with the present invention is typically refractory or responds insufficiently or is intolerant to anti-inflammatory therapy and/or demonstrates or has previously demonstrated an inadequate response, loss of response, or intolerance to at least one immunomodulator, TNF-α inhibitor or anti-integrin. Thus, typically, the subject has previously received or is currently receiving anti-inflammatory therapy, preferably anti-inflammatory therapy for UC and/or immunomodulatory, TNF-α inhibitor or anti-integrin therapy, preferably such therapy for UC. Anti-inflammatory therapies for UC are discussed herein and typically include GCS, sulfasalazine and 5-ASA.

Immunomodulators, TNF-α inhibitors and anti-integrins are discussed herein and typically include azathioprine, 6-mercaptopurine and biologicals including the TNF-α inhibitors infliximab and biosimilars and derivatives thereof, golimumab and biosimilars and derivatives thereof, adalimumab and biosimilars and derivatives thereof and anti-integrins vedolizumab and biosimilars and derivatives thereof.

A refractory disease or disease that responds insufficiently to therapy is typically a disease where signs and symptoms of active disease persist despite a history of at least one course of therapy, anti-inflammatory therapy in the context of the present invention. Typically in the context of treatment of UC, signs and symptoms of active disease persist despite a history of two or more courses of anti-inflammatory therapy. A typical course of treatment with anti-inflammatory therapy for UC would be well understood by a person skilled in the art, and would typically involve a sufficient number of doses at sufficient dosage to induce remission in a typical patient.

Intolerance to therapy, anti-inflammatory therapy in the context of the present invention, means that the therapy has caused side effects in the subject that are not tolerated, e.g. that typically lead to discontinuation of therapy.

Typically, the subject has previously received or is currently receiving Aminosalicylic acid (5-ASA), preferably 5-ASA therapy for UC.

Typically, the subject has previously received or is currently receiving oral Glucocorticosteroids (GCS), preferably oral GCS therapy for UC.

Typically, the subject who is refractory or responds insufficiently or is intolerant to anti-inflammatory therapy shows or has previously shown an inadequate response to, or loss of response to (i.e. is refractory to) or intolerance of rectal, oral, and/or parenteral GCS treatment (including no GCS treatment due to earlier side effect).

Typically, the subject who is refractory or responds insufficiently or is intolerant to anti-inflammatory therapy has a history of or current status of an inadequate response (e.g. steroid refractory) to, OR steroid dependency, OR loss of response to, OR intolerance of GCS treatment. The steroids/GCS will typically have been received by the subject in the course of treating ulcerative colitis.

Steroid-refractory typically refers to a subject lacking a meaningful clinical response, i.e. showing signs and symptoms of persistently active ulcerative colitis, despite a history of at least one course of steroid treatment, for instance an induction regimen that included a dose equivalent to prednisone 40-60 mg daily over a period of 30 days for oral administration or over a period of 7 to 10 days for intravenous (IV) administration.

Steroid dependence typically refers to a patient who is either unable to reduce steroids below the equivalent of prednisolone 10 mg/d within 3 months of starting steroids, without recurrent active ulcerative colitis, or who has a relapse within 3 months of stopping steroids.

Intolerance of GCS treatment typically means the subject has experienced side effects not tolerated by the subject following GCS treatment, such as but not limited to Cushing's syndrome, osteopenia/osteoporosis, hyperglycemia, insomnia, or infection.

An inadequate response, or loss of response to an immunomodulator typically means signs and symptoms of active ulcerative colitis persist despite previous treatment with at least one immunomodulator, for instance one 8 Week regimen of oral azathioprine (≥1.5 mg/kg) or 6-mercaptopurine (≥0.75 mg/kg).

Intolerance to an immunomodulator typically means the subject has experienced nausea/vomiting, abdominal pain, pancreatitis, liver function test (LFT) abnormalities, lymphopenia, Thiopurine Methyltransferase (TPMT) genetic mutation, or infection or other side effects after receiving an immunomodulator.

An inadequate response, or loss of response to a TNF-α inhibitor means signs and symptoms of active ulcerative colitis persist despite previous treatment with at least one TNF-α inhibitor, such as 4-Week induction regimen (or doses as recommended according to the current labels) of infliximab (5 mg/kg (IV), 2 doses at least 2 weeks apart) or a biosimilar or derivative thereof; golimumab (200/100 mg (SC), 2 doses at least 2 weeks apart) or a biosimilar or derivative thereof; or adalimumab (160/80 mg (SC), 2 doses at least 2 weeks apart) or a biosimilar or derivative thereof or recurrence of symptoms during maintenance dosing following prior clinical benefit.

Intolerance to a TNF-α inhibitor means an infusion-related reaction, demyelination, congestive heart failure, infection or other side effects following receipt of a TNF-α inhibitor.

An inadequate response, or loss of response to an anti-integrin means signs and symptoms of active ulcerative colitis persist despite previous treatment with an anti-integrin, for instance at least 10 weeks regimen of vedolizumab 300 mg (IV) or a biosimilar or derivative thereof, or as recommended in the current label, or recurrence of symptoms during maintenance dosing following prior clinical benefit.

Typically, the subject has been diagnosed with left sided ulcerative colitis, i.e. distal colitis, including proctosigmoiditis.

Typically, said subject is elective for colectomy.

As used herein, the term "colectomy" refers to surgical resection of any extent of the large intestine (colon). Herein, colectomy includes, but is not limited to, right hemicolectomy, left hemicolectomy, extended hemicolectomy, transverse colectomy, sigmoidectomy, proctosigmoidectomy, Hartmann operation, "double-barrel" or Mikulicz colostomy, total colectomy (also known as Lane's Operation), total procto-colectomy and subtotal colectomy. As used herein, the phrase "elective for colectomy" refers to a subject who may choose to undergo the procedure of non-emergency colectomy based on physician and surgeon assessment. Subjects elective for colectomy may be, but are not limited to, subjects refractory to available therapy (for ulcerative colitis) or intolerant of available therapy (for ulcerative colitis). This differs from emergency colectomy, which is an acute intervention for subjects with acute illnesses or injuries and who require immediate medical attention. The phrase also includes subjects that are elected for colectomy.

As used herein, the term "oligonucleotide" refers to a polynucleoside formed from a plurality of linked individual nucleoside units. Such oligonucleotides can be obtained from existing nucleic acid sources, including genomic DNA or cDNA, plasmids, vectors, or bacterial DNA, but are preferably produced by synthetic methods. The nucleoside residues can be coupled to each other by any of the numerous known internucleoside linkages. Such internucleoside linkages include, without limitation, the natural internucleoside phosphodiester bond or indeed modified internucleosides such as, but not limited to, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkages (e. g., (Rp)- or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholine-backbone oligonucleotides, and oligonucleotides having backbone sections with alkyl linkers or amino linkers. The alkyl linker may be branched or unbranched, substituted or unsubstituted, and chirally pure or a racemic mixture.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside, an arabinonucleoside or a 2'-deoxy-2'-substituted-arabinoside.

As used herein, the term "a hybrid oligonucleotide" is an oligonucleotide having more than one type of nucleoside.

Herein, the term "oligonucleotide" includes hybrid and chimeric oligonucleotides. A "chimeric oligonucleotide" is an oligonucleotide having more than one type of internucleoside linkage within its sequence structure. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (U.S. Pat. Nos. 5,635,377 and 5,366,878).

Herein, the term "oligonucleotide" also includes circularized variants and circular oligonucleotides.

Preferably, the oligonucleotide comprises at least one naturally occurring phosphodiester, or one modified phosphorothioate, or phosphorodithioate internucleoside linkage, however preferred linkages or indeed backbone modifications including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, 2' OMe (OxyMethyl group at 2'position), N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e. g., (Rp)- or (Sp)-phosphorothioate, alkylphosphonate, or phosphotriester linkages) are also envisaged.

The sugar moiety of the nucleoside can be a non-naturally occurring sugar moiety. Herein, a "naturally occurring sugar moiety" is a sugar moiety that occurs naturally as part of a nucleic acid, e. g., ribose and 2'-deoxyribose, and a "non-naturally occurring sugar moiety" is any sugar that does not occur naturally as part of a nucleic acid, but which can be used in the backbone for an oligonucleotide, for example but not limited to hexose. Arabinose and arabinose derivatives are examples of preferred sugar moieties.

Modified or substituted oligonucleotides are often preferred over native forms because of desirable properties such as, for example, enhanced cellular uptake, enhanced affinity for nucleic acid target and increased stability in the presence of nucleases. An oligonucleotide is usually comprised of more than ten (10) and up to one hundred (100) or more deoxyribonucleotides or ribonucelotides, although preferably between about eight (8) and about forty (40), most preferably between about eight (8) and about twenty (20). The exact size will depend on many factors, which in turn depends on the ultimate function or use of the oligonucleotide. The oligonucleotide may be generated in any manner, including chemical synthesis, DNA replication, reverse transcription, or a combination thereof.

The oligonucleotide for use in the present invention comprises the sequence 5'-GGAACAGTTCGTCCATGGC-3' (SEQ ID NO:2). Typically, at least one CG dinucleotide is unmethylated.

Typically, at least one nucleotide in said oligonucleotide has a backbone modification. Typically, at least one nucleotide in said oligonucleotide has a phosphate backbone modification. The backbone modification is typically a phosphorothioate or a phosphorodithioate modification.

Phosphorothioate linkages can be illustrated with asterisks (*) in a sequence, e.g. in the sequence: 5'-G*G*A*ACAGTTCGTCCAT*G*G*C-3' (SEQ ID NO:1), wherein the CG dinucleotide is unmethylated.

Preferably, said oligonucleotide has the sequence 5'-G*G*A*ACAGTTCGTCCAT*G*G*C-3' (SEQ ID NO:1), wherein the CG dinucleotide is unmethylated. Thus, preferably said oligonucleotide is cobitolimod.

The present invention therefore preferably provides cobitolimod for use in the treatment of active ulcerative colitis as defined herein in a human subject as defined herein, wherein individual doses of an amount as defined herein of cobitolimod are administered to the subject on at least four separate occasions, wherein the separate occasions are each a week apart.

The present invention also provides cobitolimod for use in the treatment of active ulcerative colitis as defined herein in a human subject as defined herein, wherein individual doses of an amount as defined herein of cobitolimod are administered to the subject every week until the patient is in remission, for instance as defined herein.

In the therapies of the present invention, individual doses of from 100 mg to 350 mg, typically 100 mg to 150 mg, of said oligonucleotide, preferably cobitolimod, are administered. Typically, the same dosage of oligonucleotide is administered in each individual dose/administration, but different dosages may also be used.

Usually, individual doses of greater than 100 mg up to 350 mg, typically greater than 100 mg up to 150 mg, of said oligonucleotide, preferably cobitolimod, are administered.

Typically, from 101 mg to 150 mg of said oligonucleotide, preferably cobitolimod, are administered in each dose/administration, preferably from 105 mg to 145 mg, more preferably from 110 to 140, still more preferably from 115 to 135, yet more preferably from 120 to 130, even more preferably from 121 to 129, even more preferably from 122 to 128, even more preferably from 123 to 127, even more preferably from 124 to 126 mg.

Preferably, about 125 mg of said oligonucleotide, preferably cobitolimod, is administered. Thus, about 125 mg of said oligonucleotide, preferably cobitolimod, is administered every week.

In the context of dosage of an active agent, "about" as used herein means+/−10%, typically +/−5%, preferably +/−1%.

More preferably, 125 mg of said oligonucleotide, preferably cobitolimod, is administered.

Alternatively, from 175 mg to 325 mg of said oligonucleotide, preferably cobitolimod, are administered in each dose/administration, preferably from 200 mg to 300 mg, more preferably from 210 to 290, still more preferably from 220 to 280, yet more preferably from 230 to 270, even more preferably from 240 to 260, even more preferably from 245 to 255, even more preferably from 249 to 251 mg.

Preferably, about 250 mg of said oligonucleotide, preferably cobitolimod, is administered. Thus, about 250 mg of said oligonucleotide, preferably cobitolimod, is administered on each of the at least two occasions.

More preferably, 250 mg of said oligonucleotide, preferably cobitolimod, is administered.

In the therapies of the present invention, individual doses (of an amount as specified herein) of said oligonucleotide are administered to the patient on at least four separate occasions, wherein the separate occasions are each a week apart. This means that the patient does not receive any additional oligonucleotide between the specified doses/administrations a week apart. In the week long window between specified doses/administrations a week apart, the patient does not receive an oligonucleotide as defined herein, but may receive one or more additional therapeutic agents for the treatment of ulcerative colitis.

The at least four separate occasions are consecutive. Thus, each of the at least four doses follows the previous dose (spaced apart by a week). The present invention does not extend to, for example, giving a first dose, waiting a week, giving a second dose, waiting several months, giving a third dose, waiting a week, and giving a fourth dose.

Each of the at least four separate occasions is a week after the previous occasion. Thus, four separate occasions each a week apart will involve a first administration on day zero, a second administration a week after the first administration, a third administration a week after the second administration, and a fourth administration a week after the third administration.

Typically, doses (of an amount as specified herein) of said oligonucleotide are administered to the patient on, for instance, 4, 5, 6, 7, 8, 9, or 10 separate occasions, each occasion being a week after the previous occasions. Typically, doses of said oligonucleotide are administered to the patient until that patient is in remission, as defined above. In some embodiments, individual doses are administered to the subject on only four separate occasions, the separate occasions each being a week apart.

It should be understood that reference to administration on at least four separate occasions, where the separate occasions are each a week apart, refers to a single treatment regime for inducing remission. Thus, following a course of treatment in accordance with the present invention, further treatment with the oligonucleotide is not ruled out in the future, e.g. following relapse to an active disease state after remission.

In the context of a patient receiving only four doses, a first dose would be delivered at day zero, and a second dose would be delivered a week after that, a third dose would be delivered a week after that (two weeks after day zero), and a fourth dose would be delivered a week after that (three weeks after day zero).

As used herein, the term "a week apart" means in certain embodiments administration of the doses exactly 7 days apart, i.e. one dose is administered on day zero and a further dose is administered on day seven. However, it will be appreciated that minor variations from this are still within the scope of the present invention. Such minor variations may be unavoidable due to e.g. illness of the patient or unavailability of the drug. Thus, as used herein "a week apart" means administration 3-13 days, typically 4-11 days, alternatively 5-9 days, more preferably 6-8 days apart.

Thus, in certain embodiments the present invention provides an oligonucleotide, as defined herein, for use in the treatment of ulcerative colitis, as defined herein, in a human subject, as defined herein, wherein individual doses of an amount as defined herein of said oligonucleotide are administered to the patient on at least four, for instance four, separate occasions, wherein the separate occasions are each 3-13 days, typically 4-11 days, alternatively 5-9 days, preferably 6-8 days apart.

The drugs for use in the present invention may be administered as monotherapy treatment for the indication or with other drug(s) as adjunct therapy for the indication, as described in more detail below. In the case of adjunct (or "add-on") therapy, the drugs for use in the present invention may be administered simultaneously, separately or sequentially with the other drug(s), for example in fixed dose combination or in separate doses.

As used herein, the term "add-on" refers to administering of said oligonucleotide in addition to a current therapy or drug regime, without discontinuing the current therapy or drug regime.

Thus, the oligonucleotide may be administered as a monotherapy, or in combination with one or more additional therapeutic agents for the treatment of ulcerative colitis. Typically, the oligonucleotide may be administered as a monotherapy, or in combination with one or more additional therapeutic agents for the treatment of ulcerative colitis chosen from immunomodulatory drugs, anti-TNF therapy drugs or other suitable drugs for treating ulcerative colitis.

Examples of such drugs suitable for use in combination with said oligonucleotide include, but are not limited to GCS or derivatives; prednisolone, Decortin, anti-TNF or derivative; infliximab and biosimilars and derivatives thereof, adalimumab and biosimilars and derivatives thereof, golimumab and biosimilars and derivatives thereof, anti-integrin or derivatives; vedolizumab and biosimilars and derivatives thereof, natural IFN-β, thiopurine or derivatives; azathioprine, 6-mercaptopurine, 5-ASA, sulphasalazine, methotrexate, cylclosporine, and equivalents thereof.

Typically, the subject receiving said oligonucleotide also receives one or more other drugs chosen from GCS, Decortin, 5-ASA, azathioprine, 6-mercaptopurine, sulphasalazine, methotrexate, prednisolone and equivalents thereof or derivatives.

Preferably, the subject receiving said oligonucleotide also receives one or more other drugs chosen from GCS, 5-ASA, azathioprine, 6-mercaptopurine, sulphasalazine and methotrexate.

More preferably, the subject receiving said oligonucleotide also receives one or more other drugs chosen from oral GCS, oral 5-ASA, azathioprine, 6-mercaptopurine, and oral methotrexate.

In some embodiments, the subject receiving said oligonucleotide also receives one or more steroid drugs, for example corticosteroids and glucocorticosteroids.

For purposes of the invention, the terms "in combination with" and "add-on" mean in the course of treating the same disease in the same patient, and include administering the oligonucleotide and one or more additional therapeutic agents in any order, including simultaneous administration, as well as temporally spaced order of up to several months apart.

Typically, said oligonucleotide is administered topically, such as topically to the mucous membrane.

Typically, said oligonucleotide is administered intracolonically. Intracolonical administration is typically effected rectally. Intracolonical administration is typically effected using an enema or catheter. Intracolonical administration may involve administration by a rectal enema. Intracolonical administration may be topical, for example performed during colonoscopy with the aid of a spraying catheter, or other suitable medical equipment, inserted though the colonoscopies biopsy channel. The said oligonucleotide may be delivered to the upper portion of the descending colon or to the transverse region of the colon; however other regions are also possible when suited. Topical administration to other parts of the gastrointestinal tract is also possible. Yet in another embodiment of this aspect, the said oligonucleotide can be administered by any appropriate administration route, such as, but not limited to, inhalation, intranasal, parenteral, oral, intradermal, subcutaneous, vaginal and rectal administration. Further, in certain embodiments, systemic administration of said oligonucleotide may be used.

The oligonucleotide may be administered in the form of a pharmaceutical composition comprising the oligonucleotide as defined herein together with one or more pharmaceutically acceptable carriers. As used herein, the term "carrier" encompasses any excipient, diluent, filler, salt, buffer, water, stabilizer, solubilizer, lipid, or other material well known in the art for use in pharmaceutical formulations. It will be understood that the characteristics of the carrier will depend on the route of administration for a particular application.

As used herein, the term "pharmaceutically acceptable" refers to a material that does not interfere with the effectiveness of the immunomodulatory oligonucleotide and is compatible with a biological system such as a cell, cell culture, tissue, organ, or organism. Preferably, the biological system is a living organism, such as a vertebrate.

Typically, the composition is a solution of the oligonucleotide in a liquid carrier.

Typically, the carrier is water, preferably sterile water. Thus, typically the composition comprises the oligonucleotide as defined herein and water.

Preferably, the carrier is water and the oligonucleotide (in the form of a composition) is administered intracolonically, for instance as a rectal enema.

The oligonucleotide has been found to be advantageously stable in water, and it is therefore possible to administer the oligonucleotide as a composition consisting essentially of the oligonucleotide as defined herein and water. The composition may consist of the oligonucleotide as defined herein and water.

A composition consisting essentially of components refers to a composition comprising the components of which it consists essentially as well as other components, provided that the other components do not materially affect the essential characteristics of the composition. Typically, a composition consisting essentially of certain components will comprise greater than or equal to 95 wt % (relative to the total weight of the composition) of those components or greater than or equal to 99 wt % (relative to the total weight of the composition) of those components.

Thus, a composition consisting essentially of the oligonucleotide as defined herein and water comprises greater than or equal to 95 wt % of oligonucleotide and water (relative to the total weight of the composition) or greater than or equal to 99 wt % of oligonucleotide and water (relative to the total weight of the composition).

The concentration of an oligonucleotide in a pharmaceutical composition will vary depending on several factors, including the dosage of the oligonucleotide to be administered. Typical concentrations of oligonucleotides in compositions that are solutions are 1 mg/ml to 10 mg/ml, preferably 2 to 5 mg/ml, in some cases 5 to 10 mg/ml preferably 2.4 mg/ml to 2.6 mg/ml, more preferably about 2.5 mg/ml. Alternatively, concentrations of oligonucleotides in compositions that are solutions are 1 mg/ml to 20 mg/ml, preferably 4 to 10 mg/ml, in some cases 10 to 20 mg/ml, preferably 4.8 mg/ml to 5.2 mg/ml, more preferably about 5.0 mg/ml.

Preferably, the present invention provides cobitolimod for use in the treatment of ulcerative colitis, as defined herein, in a human subject, as defined herein, wherein individual doses of about 125 mg of cobitolimod are administered to the patient on only four separate occasions, the separate occasions each being a week apart.

Alternatively, the present invention provides cobitolimod for use in the treatment of ulcerative colitis, as defined herein, in a human subject, as defined herein, wherein individual doses of about 125 mg of cobitolimod are administered to the patient on four or more separate occasions, the separate occasions each being a week apart, until the subject is in remission, typically remission as determined by an index as defined herein.

More preferably the present invention provides cobitolimod for use in the treatment of active ulcerative colitis, as defined herein, in a human subject, as defined herein, wherein individual doses of about 125 mg of cobitolimod are administered to the patient on only four separate occasions, the separate occasions each being a week apart, wherein cobitolimod is administered in the form of a pharmaceutical composition comprising cobitolimod and water.

More preferably the present invention provides cobitolimod for use in the treatment of active ulcerative colitis, as defined herein, in a human subject, as defined herein, wherein individual doses of about 125 mg of cobitolimod are administered to the patient on only four separate occasions, the separate occasions each being a week apart, wherein cobitolimod is administered intracolonically or rectally.

More preferably the present invention provides cobitolimod for use in the treatment of active ulcerative colitis, as defined herein, in a human subject, as defined herein, wherein individual doses of about 125 mg of cobitolimod are administered to the patient on only four separate occasions, the separate occasions each being a week apart, wherein cobitolimod is administered intracolonically or rectally in the form of a pharmaceutical composition comprising cobitolimod and water.

Even more preferably the present invention provides cobitolimod for use in the treatment of chronic active ulcerative colitis, as defined herein, in a human subject, as defined herein, wherein individual doses of about 125 mg of cobitolimod are administered to the patient on only four separate occasions, the separate occasions each being a week apart, wherein cobitolimod is administered intracolonically or rectally in the form of a pharmaceutical composition comprising cobitolimod and water.

The present invention also provides a pharmaceutical composition comprising an oligonucleotide as defined herein, together with one or more pharmaceutically acceptable carriers, for use in the treatment of an inflammatory bowel disease as defined herein in a human subject as defined herein, wherein individual administrations of said composition are administered to the subject on at least four separate occasions, wherein the separate occasions are each a week apart, and wherein each administration of the composition delivers an amount of the oligonucleotide as defined herein.

Preferred features of the oligonucleotide for use as defined above are also preferred features of the composition for use.

The present invention also provides use of an oligonucleotide as defined herein, or a pharmaceutical composition as defined herein, in the manufacture of a medicament for use in treating an inflammatory bowel disease as defined herein, in a human subject as defined herein, wherein individual administrations of said oligonucleotide or composition are administered to the patient on at least four separate occasions, wherein the separate occasions are each a week apart, and wherein each administration of the oligonucleotide or composition delivers an amount of the oligonucleotide as defined herein.

Preferred features of the oligonucleotide for use as defined above are also preferred features of the use of the oligonucleotide or composition.

The present invention also provides a method of treating an inflammatory bowel disease as defined herein, in a human subject as defined herein, comprising administering to said subject an oligonucleotide as defined herein or a composition as defined herein, wherein individual administrations of said oligonucleotide or composition are administered to the patient on at least four separate occasions, wherein the separate occasions are each a week apart, and wherein each administration of the oligonucleotide or composition delivers an amount of the oligonucleotide as defined herein.

The present invention also provides a method of treating an inflammatory bowel disease as defined herein, in a human subject as defined herein, which method comprises:
(a) selecting a patient as defined herein; and
(b) administering to said patient an oligonucleotide as defined herein or a composition as defined herein, wherein individual administrations of said oligonucleotide or composition are administered to the patient on at least four separate occasions, wherein the separate occasions are each a week apart, and wherein each administration of the oligonucleotide or composition delivers an amount of the oligonucleotide as defined herein.

Preferred features of the oligonucleotide for use as defined above are also preferred features of the claimed method.

The following non-limiting Examples illustrate the invention.

EXAMPLES

Example 1—Clinical Trial Study

A randomised double-blind, placebo controlled, trial assesses the efficacy and safety of topical cobitolimod in moderate to severe active ulcerative colitis patients in accordance with established methods.

Methods: Men and women are selected for trial according to standard inclusion criteria in the field including the following:

1. Male or female≥18 years of age
2. Established diagnosis of UC, with minimum time from diagnosis of ≥3 months
3. Moderately to severely active left sided UC (disease should extend 15 cm or more above the anal verge and not beyond the splenic flexure) determined by a Modified Mayo score (excluding the friability at grade 1 for the endoscopic sub score) of 6 to 12 with an endoscopic sub score≥2 assessed by central reading of endoscopy performed at screening visit 1b (Day −7 to −10—screening visit), and no other individual sub score<1
4. Current oral 5-ASA/SP use or a history of oral 5-ASA/SP use
5. Current GCS use or history of GCS dependency, refractory, or intolerance, including no GCS treatment due to earlier side-effects (only one of the GCS criteria have to be fulfilled, see definition in European Crohn's and Colitis organisation (ECCO) guidelines)
6. Demonstrated an inadequate response, loss of response, or intolerance to at least one of the following agents:
    Immunomodulators, e.g. cyclosporine, methotrexate, AZA/6-MP, tacrolimus
        For example, signs and symptoms of persistently active disease despite previous treatment with at least one 8 week regimen of oral AZA (≥1.5 mg/kg) or 6-MP (≥0.75 mg/kg) or lower doses prompted by intolerance or thiopurine methyltransferase (TPMT) deficiency or
        For example, previous intolerance (including, but not limited to, nausea/vomiting, abdominal pain, pancreatitis, liver function test (LFT) abnormalities, lymphopenia, TPMT genetic mutation, infection) to at least one immunomodulator
    TNF-α inhibitors and/or anti-integrins:
        Signs and symptoms of persistently active disease despite previous treatment with at least one induction regimen with 2 doses at least 2 weeks apart (or doses as recommended according to the current labels) of for e.g.:
            Infliximab 5 mg/kg (intravenous (IV)) or
            Golimumab 200/100 mg (subcutaneous (SC)) or
            Adalimumab 160/80 mg (SC) or
            Vedolizumab 300 mg (IV) or
        History of intolerance (including but not limited to infusion-related reaction, demyelination, congestive heart failure, infection)
    Recurrence of symptoms during maintenance dosing with any of the above medications following prior clinical benefit, (secondary failure) [discontinuation despite clinical benefit does not qualify]
7. Allowed to receive a therapeutic dose of following UC drugs during the study:
    a) Oral GCS therapy (≤20 mg prednisone or equivalent/daily) providing that the dose has been stable for 2 weeks prior to visit 1a (Day −14)
    b) Oral MMX Budesonide therapy (9 mg/daily) initiated at least 8 weeks before visit 1a
    c) Oral 5-ASA/SP compounds, providing that the dose has been stable for 2 weeks prior to visit 1a and initiated at least 8 weeks before visit 1a d) AZA/6-MP providing that the dose has been stable for 8 weeks prior to visit 1b and been initiated at least 3 months before visit 1a
8. Ability to understand the treatment, willingness to comply with all study requirements and ability to provide informed consent Patients may be excluded from trial in accordance with known exclusion criteria in the field including the following:
1. Suspicion of differential diagnosis such as; Crohn's enterocolitis, ischaemic colitis, radiation colitis, indeterminate colitis, infectious colitis, diverticular disease, associated colitis, microscopic colitis, massive pseudopolyposis or non-passable stenosis
2. Acute fulminant UC and/or signs of systemic toxicity
3. UC limited to the rectum (disease which extend <15 cm above the anal verge)
4. History of malignancy, except for:
   Treated (cured) basal cell or squamous cell in situ carcinoma
   Treated (cured) cervical intraepithelial neoplasia or carcinoma in situ of the cervix with no evidence of recurrence within the previous 5 years prior to the screening visit 1a
5. History or presence of any clinically significant disorder that, in opinion of the investigator, could impact on patient's possibility to adhere to the protocol and protocol procedures or would confound the study result or compromise patient safety
6. Concomitant treatment with cyclosporine, methotrexate, tacrolimus, TNF-α inhibitors, anti-integrins or similar immunosuppressants and immunomodulators at enrolment. Any prior treatment with such drugs must have been discontinued at least 8 weeks prior to visit 1a or have non-measurable serum concentration levels
7. Treatment with rectal GCS, 5-ASA/SP or tacrolimus within 2 Weeks before visit 1b
8. Long term treatment with antibiotics or non-steroidal anti-inflammatory drugs (NSAIDs) within two weeks prior to visit 1a (one short treatment regime for antibiotics and occasional use of NSAIDS are allowed)
9. Serious active infection
10. Gastrointestinal infections including positive *Clostridium difficile* stool assay
11. Currently receiving parenteral nutrition or blood transfusions
12. Females who are lactating or have a positive serum pregnancy test during the screening period
13. Women of childbearing potential not using reliable contraceptive methods (reliable methods are barrier protection, hormonal contraception, intra-uterine device or abstinence) throughout the duration of the study
14. Concurrent participation in another clinical study with investigational therapy or previous use of investigational therapy within 5 half-lives and within at least 30 days after last treatment of the experimental product prior to enrolment
15. Previous exposure to cobitolimod Patients selected for trial are randomised to treatment sequences comprising cobitolimod at effective dosage (including a group receiving four administrations of 125 mg cobitolimod each a week apart (Week zero, week 1, week 2, week 3)) and placebo administered rectally by rectal enema.

Trial endpoints/assessed clinical criteria are as follows:
Proportion of patients with induction of clinical remission, symptomatic remission, endoscopic remission or (complete) histological remission at Week 4 or 6
Proportion of patients with absence of rectal bleeding at Week 4 or 6
Proportion of patients with normal or enhanced stool frequency at Week 4 or 6
Proportion of patients with induction of durable symptomatic remission at Week 6 and Week 10
Proportion of patients in clinical response at Week 6
Proportion of patients with histological response at Week 6
Proportion of patients with reduced defecation urgency score
Mean change in faecal calprotectin at Week 1, 2, 3, and 6 compared to Week 0
Mean change in steroid dosage for patients in remission at Week 6 to Week 10
Mean change in each of the inflammatory bowel disease questionnaire (IBDQ) sub domains at Week 6 compared to Week 0
Proportion of patients with endoscopic and histological remission at Week 6

Conclusion: Treatment with four doses of 125 mg cobitolimod each a week apart in patients suffering from moderate to severe ulcerative colitis leads to improved clinical effects indicating usefulness of cobitolimod in treating ulcerative colitis.

Example 2—Dextran Sulfate Sodium (DSS) Induced Colitis Mouse Model

Materials and Methods
Mice:
Balb/c mice were obtained from Charles River Laboratories, Research Models and Services (Sulzfeld, Germany). Eight week old female Balb/c mice were used for the experiments and were kept in individually ventilated cages in compliance to the Animal Welfare Act. Water and food were available ad libitum.

DSS Induced Colitis:
3% (w/v) Dextran sulfate sodium (DSS) (MP Biomedicals, Illkirch, France) was administered for 10 days to the drinking water of 8 week old female Balb/c mice. An additional control group of three mice which were completely untreated was also part of the experimental set up. Food uptake and bodyweight were monitored on days 0, 2, 4, 6, 7, 8, and 10.

Rectal Administration of Cobitolimod:
40 µg, 84 µg, or 1560 µg cobitolimod per mouse was rectally administered twice (on days 4 and 8). 500 µg cobitolimod per mouse was rectally administered four times (on days 4, 5, 6 and 8). The respective concentration of cobitolimod was diluted with sterile water and 100 µl per mouse was used for rectal administration. A dose of 500 µg in mice is approximately equivalent to a 125 mg dose in a human (see "*Guidance for Industry—Estimating the Maximum Safe Starting Dose in Initial Clinical Trials for Therapeutics in Adult Health Volunteers*", US Department of Health and Human Services Food and Drug Administration Center for Drug Evaluation and Research, July 2005). The results observed in this mouse model could be considered predictive of the effects observed in humans administered with individual doses of from 100 mg to 150 mg of cobitolimod on four separate occasions, each a week apart. The dose of 84 µg in mice is broadly equivalent to a dose of 30 mg in humans.

Sterile water without cobitolimod was additionally rectally applied to a control group of seven mice (placebo). Mice from different treated groups were randomly mixed per cage before initiation of the experiment to ensure comparable experimental conditions.

Evaluation of DSS Induced Colitis:

Loss of bodyweight was monitored on the days 0, 2, 4, 6, 7, 8 and 10. The Disease Activity Index (DAI) is the combined score of body weight loss compared to initial body weight, stool consistency, and visible blood in feces. The maximum score per mouse is 12. The DAI was assessed on the days 0, 2, 4, 6, 7, 8 and 10. Additionally, colon inflammation was studied in vivo using the Coloview endoscopic system consisting of a miniature endoscope (scope 1.9 mm outer diameter), a xenon light source, a triple chip camera and an air pump (all from Karl Storz, Tutzingen, Germany) to achieve regulated inflation of the mouse colon. For endoscopy mice were anesthetized with 4% of isoflurane in 100% oxygen at a rate of 0.2-0.5 L/mins, 2% isoflurane was used for maintenance. The endoscopic colitis grading consists of the five parameters: thickening of the colon, change of the normal vascular pattern, presence of fibrin, mucosal granularity and stool consistency. Endoscopic grading was performed for each parameter (score 0-3) leading to an accumulative score between 0-15. Endoscopic grading was analyzed on days 0, 2, 4, 6, 7, 8 and 10.

Results

FIG. 1 shows the change in body weight of the mice in the various treatment groups over the course of the experiment. Four days after initiation of DSS treatment all DSS treated groups started to lose weight in a comparable way. Rectal application of cobitolimod resulted in a significant reduction in weight loss at day 6 in mice treated with 84 µg cobitolimod and 500 µg cobitolimod compared to placebo treated mice.

At day 7, weight loss was more significantly reduced in the group treated with 500 µg cobitolimod (**P=0.0012) compared to the group treated with 84 µg cobitolimod (*P=0.0122) and thereafter the weight loss in both groups continued to be significantly less than that in the placebo treated group up until day 10 (the end of the experiment).

No significant reduction in weight loss was noted for the group treated with 40 µg cobitolimod compared to the placebo group. The group treated with 1560 µg cobitolimod showed increased weight loss compared to placebo treated mice. At the end of the experiment on day 10, all cobitolimod treated groups show reduced weight loss compared to the placebo treated group, apart from the group treated with 1560 µg cobitolimod which showed similar weight loss to that of the placebo treated group. The body weight of mice which were completely untreated (no DSS, no cobitolimod/placebo) did not change throughout the experiment (FIG. 1).

Figure 2:
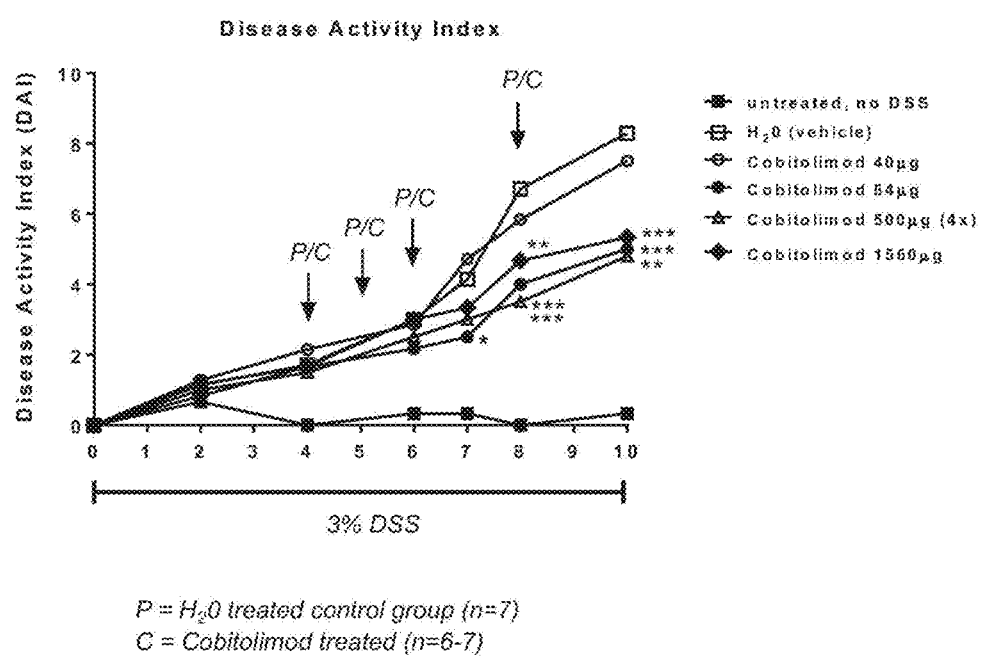
FIG. 2 shows the results for disease activity index (DAI) in a DSS-induced colitis mouse model over 10 days.

FIG. 2 shows the change in disease activity index (DAI) of the mice in the various treatment groups over the course of the experiment. The DAI data also revealed that rectal application of cobitolimod ameliorates DSS induced colitis. All cobitolimod treated mice show similar changes in the DAI except for 40 µg cobitolimod treated mice. The mice group treated with 40 µg cobitolimod did not exhibit a significant reduction in DAI compared to the placebo control. Mice treated with 84 µg and 500 µg of cobitolimod showed a reduction in DAI from day 6 until the end of the experiment compared to placebo treated mice with a significant reduction in DAI noted at days 8 and 10 (*P=0.0006). The mice group treated with 1560 µg of cobitolimod show a reduced DAI at day 7 and at day 8 and 10 the reduction was significant (P=0.0023 and ***P=0.0006, respectively). The DAI of mice which were completely untreated (no DSS, no cobitolimod/placebo) did not change throughout the experiment (FIG. 2).

Figure 3:
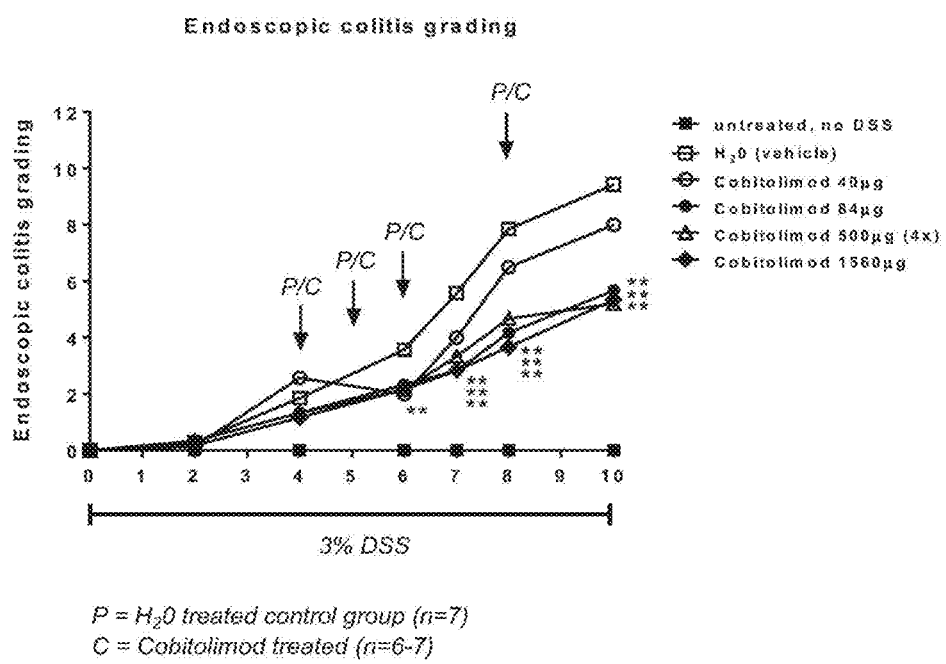
FIG. 3 shows the results for endoscopic colitis grading in a DSS-induced colitis mouse model over 10 days.

FIG. 3 shows the change in endoscopic colitis grading of the mice in the various treatment groups over the course of the experiment. The endoscopic colitis grading is consistent with the results for weight loss and DAI. All mice treated with cobitolimod developed fewer signs of DSS induced colitis compared to the placebo treated group. The endoscopic colitis grading compared to the placebo group reduced after the first application of cobitolimod until the end of the experiment for all cobitolimod treated groups. The reduction was significant (**P≤0.01) from day 7 for all cobitolimod treated groups except for 40 µg cobitolimod treated group (FIG. 3).

Conclusion

Taken together, these results show that cobitolimod treatment ameliorated DSS-induced colitis, by significantly reduced the weight loss, disease activity index and endoscopic colitis grade of the mice. In particular, in the mice that were administered 500 µg of cobitolimod at days 4, 5, 6 and 8, significant improvements for weight loss, DAI and endoscopic colitis grading were achieved.

Example 3—Flow Cytometry Results for Dextran Sulfate Sodium (DSS) Induced Colitis Mouse Model Materials and Methods Mice:

Balb/c mice were obtained from Charles River Laboratories, Research Models and Services (Sulzfeld, Germany). Eight week old female Balb/c mice were used for the experiments and were kept in individually ventilated cages in compliance to the Animal Welfare Act. Water and food were available ad libitum.

DSS Induced Colitis:

3% (w/v) Dextran sulfate sodium (DSS) (MP Biomedicals, Illkirch, France) was administrated for 10 days to the drinking water of 8 week old female Balb/c mice. An additional control group of three mice which were completely untreated was also part of the experimental set up.

Rectal Administration of Cobitolimod:

40 µg, 84 µg, 500 µg or 1560 µg cobitolimod per mouse was administered rectally twice (on days 4 and 8). The respective concentration of cobitolimod was diluted with sterile water and 100 µl per mouse was used for rectal administration. A dose of 500 µg in mice is approximately equivalent to a 125 mg dose in a human (human equivalent dose, HED—see "Guidance for Industry—Estimating the Maximum Safe Starting Dose in Initial Clinical Trials for Therapeutics in Adult Health Volunteers", US Department of Health and Human Services Food and Drug Administration Center for Drug Evaluation and Research, July 2005). The dose of 84 µg in mice is broadly equivalent to a dose of 30 mg in humans.

Sterile water without cobitolimod was additionally rectally applied to a control group of seven mice (placebo). Mice from different treated groups were randomly mixed per cage before initiation of the experiment to ensure comparable experimental conditions.

Flow Cytometry:

Mice were sacrificed via cervical dislocation on day 10 and colon specimens were taken for flow cytometry analysis. Lamina propria mononuclear cells (LPMCs) from gut specimen were isolated using the lamina propria kit (Miltenyi Biotec, Bergisch Gladbach, Germany). Prior to intracellular staining, cells were treated with a stimulation cocktail containing PMA, Golgi-Stop and Ionomycin (eBioscience, Frankfurt, Germany) for 4 hours at 37° C. Cells were fixed and permeabilized using a transcription factor buffer set (BD Biosciences, Heidelberg, Germany). Cells were stained for CD4 (BD Pharmingen, Franklin, USA), IL17A (Biolegend, San Diego, USA), RoryT (BD Pharmingen, Franklin, USA), and respective isotype controls. For myeloid-derived suppressor cells (MDSCs), isolated LPMCs were extracellularly stained for CD11b (Miltenyi Biotec, Bergisch Gladbach, Germany) and Gr-1 (BD Pharmingen, Franklin, USA). Flow cytometry analysis was performed with FACS Calibur (BD Biosciences, Heidelberg, Germany). Cells were analyzed using the FlowJo single cell analysis software (Version 10.1r5, TreeStar Ashland, USA).

Statistical Analysis:

Statistical analysis was performed using Graph Pad Prism (Graph Pad Software Version 6.05, La Jolla, Calif.). After testing for normal distribution with the Shapiro Wilk normality test, significant differences between samples were calculated using the unpaired Student's t test or the Mann-Whitney U-rank test (*P≤0.05; P≤0.01; *P≤0.001).

Results

Figure 4:
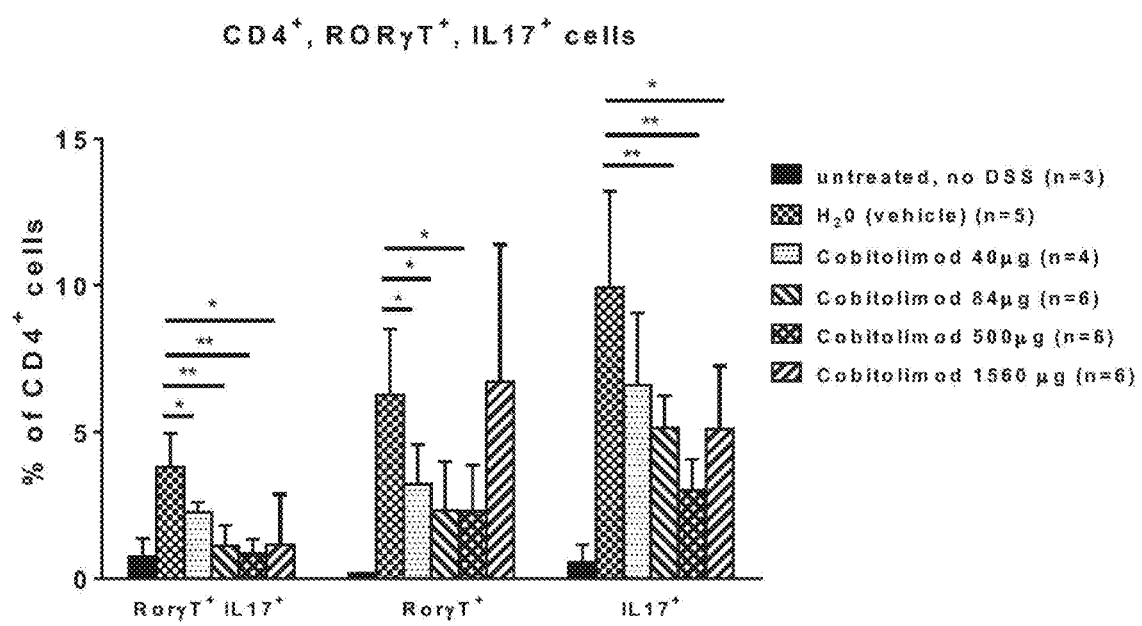
FIG. 4 shows flow cytometry analysis showing percentage of IL17$^+$, RORγT$^+$, and IL17$^+$ROR γT$^+$ cells in CD4$^+$ T cell subset of the Lamina propria mononuclear cells (LPMCs) isolated from mouse colon specimens in a DSS induced colitis mouse model at day 10.

FIG. 4 shows the results of intracellular staining of LPMCs in colon samples harvested from the mice on day 10. Classically, IBD was thought to be primarily mediated by Th1 cells in CD or Th2 cells in UC, but it is now known that Th17 cells and their related cytokines are crucial mediators in both conditions. Th17 cells massively infiltrate the inflamed intestine of IBD patients, where they produce IL17A and other cytokines, triggering and amplifying the inflammatory process (Gálvez J., *Role of Th17 Cells in the Pathogenesis of Human IBD*. ISRN Inflamm. 2014 Mar. 25; 2014:928461). It has been shown that the levels of IL17/Th17 were significantly higher in serum/colon of UC patients compared with healthy control subjects (Gong, Y., et al., *The Th17/Treg immune balance in ulcerative colitis patients with two different chinese syndromes: dampness-heat in large intestine and spleen and kidney yang deficiency syndrome*. Evid Based Complement Alternat Med. 2015: p. 264317). Therefore, reduction of Th17 and IL17 is an important step to improve clinical end points in IBD patients.

The colonic LPMCs were stained for the presence of Th17 cells and transcription factor retinoic acid receptor-related orphan receptor gamma t (RORγt, the transcription factor that regulates Th17 differentiation). As expected, the Th17 (RORγt$^+$, IL17$^+$), RORγt$^+$, and IL17$^+$ cell populations were increased in mice suffering from colitis (DSS treated) as compared to healthy animals (controls, no DSS). This increase was significantly dampened after cobitolimod treatment compared to water treatment. Flow cytometry analysis of LPMCs isolated from mouse colon specimens taken at the end of the experiment on day 10 revealed significantly reduced levels of RoryT$^+$IL17$^+$, RoryT$^+$ and IL17$^+$ T-cells in cobitolimod treated mice compared to placebo treated mice. The reduction of CD4$^+$IL17$^+$ cells was more pronounced in the 500 µg cobitolimod treated group than in the other groups (FIG. 4).

Figure 5:
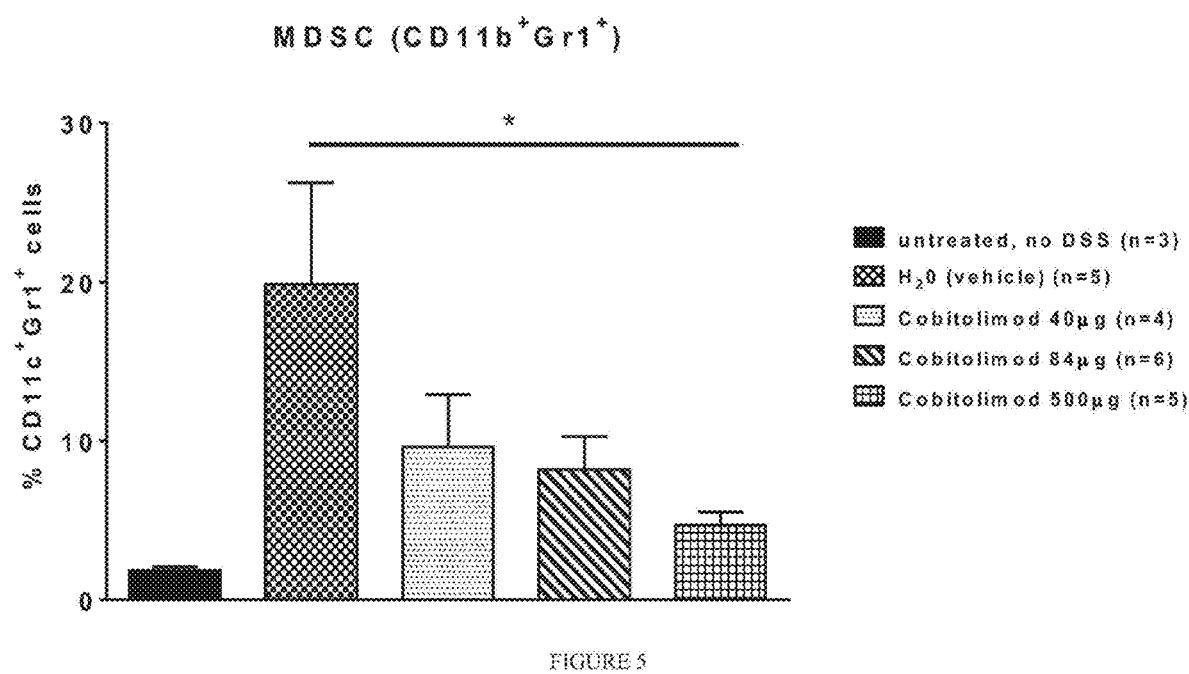
FIG. 5 shows flow cytometry analysis of the Myeloid derived suppressor cell (MDSC CD11$^+$Gr1$^+$) population isolated from the mouse colon specimens in a DSS induced colitis mouse model at day 10.

FIG. 5 shows flow cytometry analysis showing the percentage of Myeloid derived suppressor cells (CD11$^+$Gr1$^+$) present in the Lamina propria mononuclear cells (LPMCs) isolated from mouse colons on day 10.

Myeloid cells are the most abundant and heterogeneous population of leukocytes. They are rapidly recruited from the blood to areas of inflammation and perform a number of important biological functions. Chronic inflammatory conditions contribute to generation of myeloid-derived suppressor cells (MDSCs). These pathologically activated cells are increasingly recognized as important players in cancer and IBD. The role of MDSCs in IBD is still controversial, however it has been shown that MDSCs induced by intestinal inflammation conditions might be involved in Th17 generation and IL17 production and establishing the pro-inflammatory environment thereby playing a role in the pathogenesis of IBD (reviewed in Yeon-Jeong Kim., et al., *Myeloid-Derived Suppressor Cells in Inflammatory Bowel Disease*. Intest. Res. 2015: 13(2): 105-111). Therefore, reduction of MDSCs can contribute to the treatment of intestinal inflammation in IBD patients.

Further analysis revealed elevated levels of Gr1$^+$CD11b$^+$ MDSCs in placebo treated mice compared to cobitolimod treated mice. Mice treated with 500 µg cobitolimod significantly (*P≤0.05) down regulated the level of Gr1$^+$CD11b$^+$ MDSCs (FIG. 5). The reduction in Gr1$^+$CD11b$^+$ MDSC population was most pronounced for the mice administered 500 µg of cobitolimod.

CONCLUSION

These results show that cobitolimod treatment significantly reduced the pro-inflammatory IL17+ mucosal T-cells and the Gr1$^+$CD11b$^+$ MDSC population in the colons of mice in the DSS-induced colitis model. These mice also showed the most promising results in the samples taken from the colons (reduction in IL17+ CD4+ cells and Gr1$^+$CD11b$^+$ MDSC population). Surprisingly, the reduction in IL17+ CD4+ cells for the 500 µg dose is greater than that for the 84 µg and 1560 µg doses, suggesting that dosages between these values are most effective in modulating the immune response in IBD. This finding also suggests that, in humans, a dosage regime of from 100 mg to 150 mg of cobitolimod on at least four separate occasions a week apart would be better able to modulate the immune response than other higher and lower doses, and would therefore be particularly effective for treating IBD.

The invention claimed is:

1. A method of treating moderate-to-severe active ulcerative colitis in a human subject comprising administering to said subject an oligonucleotide comprising the sequence 5'-GGAACAGTTCGTCCATGGC-3' (SEQ ID NO:2), wherein individual doses of from 100 mg to 350 mg of said oligonucleotide are administered to the subject on at least four separate occasions, wherein the separate occasions are each a week apart, wherein said subject is refractory or responds insufficiently or is intolerant to anti-inflammatory therapy and/or wherein said subject is elective for colectomy.

2. The method according to claim 1, wherein said active ulcerative colitis is chronic active ulcerative colitis.

3. The method according to claim 1, wherein at least one CG dinucleotide is unmethylated, and/or wherein at least one nucleotide in said oligonucleotide has a backbone modification.

4. The method according to claim 3, wherein said backbone modification is a phosphate backbone modification represented by a phosphorothioate or a phosphorodithioate modification.

5. The method according to claim 1, wherein said oligonucleotide has the sequence 5'-GGAACAGTTCGTCCATGGC-3' (SEQ ID NO:2), wherein the CG dinucleotide is unmethylated.

6. The method according to claim 1, wherein said oligonucleotide has the sequence 5'-G*G*A*ACAGTTCGTCCAT*G*G*C-3' (SEQ ID NO: 1), wherein the CG dinucleotide is unmethylated, and wherein * represents a phosphorothioate linkage.

7. The method according to claim 1, wherein individual doses of 100 mg to 150 mg of said oligonucleotide are administered.

8. The method according to claim 1, wherein individual doses of about 125 mg of said oligonucleotide are administered.

9. The method according to claim 1, wherein (a) individual doses of said oligonucleotide are administered to the subject on only four separate occasions, wherein the separate occasions are each a week apart, or (b) individual doses of said oligonucleotide are administered to the subject on at least four separate occasions, wherein the separate occasions are each a week apart, until the subject is in remission.

10. The method according to claim 1, wherein the subject receives one or more additional therapeutic agents for the treatment of an inflammatory bowel disease.

11. The method according to claim 1, wherein said oligonucleotide is administered topically to mucosal membranes.

12. The method according to claim 1, wherein said oligonucleotide is administered rectally.

13. The method according to claim 1, wherein the oligonucleotide is cobitolimod, and individual doses of about 125 mg of cobitolimod are administered to the subject on only four separate occasions, wherein the separate occasions are each a week apart.

14. A method of treating moderate-to-severe active ulcerative colitis in a human subject, comprising administering to said subject a pharmaceutical composition comprising an oligonucleotide comprising the sequence 5'-GGAACAGTTCGTCCATGGC-3' (SEQ ID NO:2), together with one or more pharmaceutically acceptable carriers, wherein individual administrations of said composition are administered to the subject on at least four separate occasions, wherein the separate occasions are each a week apart, and wherein each administration of the composition delivers an amount of from 100 mg to 350 mg of said oligonucleotide, wherein said subject is refractory or responds insufficiently or is intolerant to anti-inflammatory therapy and/or wherein said subject is elective for colectomy.

15. The method according to claim 14, wherein the pharmaceutically acceptable carrier is water.

16. The method according to claim 14, wherein the pharmaceutically acceptable carrier is a buffer.

17. A method of treating moderate-to-severe active ulcerative colitis in a human subject, comprising administering to said subject a pharmaceutical composition comprising an oligonucleotide comprising the sequence 5'-GGAACAGTTCGTCCATGGC-3' (SEQ ID NO:2), wherein individual doses of from 100 mg to 350 mg of said oligonucleotide are administered to the subject every week until the subject is in remission, wherein said subject is refractory or responds insufficiently or is intolerant to anti-inflammatory therapy and/or wherein said subject is elective for colectomy.

18. The method according to claim 1, wherein said oligonucleotide is cobitolimod.

19. The method according to claim 10, wherein the subject receives one or more additional therapeutic agents for the treatment of ulcerative colitis.

\* \* \* \* \*